United States Patent [19]

Kleemann et al.

[11] 4,390,706

[45] Jun. 28, 1983

[54] PROCESS FOR THE RECOVERY OF PURE NITRILES

[75] Inventors: Axel Kleemann, Hanau; Peter M. Schalke, Seligenstadt, both of Fed. Rep. of Germany

[73] Assignee: Degussa Aktiengesellschaft, Frankfurt, Fed. Rep. of Germany

[21] Appl. No.: 235,985

[22] Filed: Feb. 19, 1981

[30] Foreign Application Priority Data

Feb. 21, 1980 [DE] Fed. Rep. of Germany ....... 3006424

[51] Int. Cl.$^3$ .................. C07D 333/24; C07C 121/66
[52] U.S. Cl. ................................ 349/74; 260/465 C; 260/465 F; 260/465 G; 260/465H
[58] Field of Search ........... 260/465 C, 465 F, 465 G, 260/465 H; 549/74

[56] References Cited

U.S. PATENT DOCUMENTS 2,553,404  5/1951  Dixon .
2,606,917  8/1952  Dixon .
3,936,486  2/1976  Egger et al. ................ 260/465.8 R

FOREIGN PATENT DOCUMENTS 2037762  7/1980  United Kingdom .

OTHER PUBLICATIONS

Grimm et al., Ind. Eng. Chem. Prod. Res. Div. vol. 14, (1975), No. 3, pp. 158-161.

Primary Examiner—Dolph H. Torrence
Attorney, Agent, or Firm—Cushman, Darby & Cushman

[57] ABSTRACT

The recovery from the reaction gases of aromatic or heteroaromatic nitriles which are formed in the reaction of cyanogen chloride with aromatic or heteroaromatic methylene or methyl compounds is undertaken by partial condensation of the reaction gases with decreasing temperature steps. Through this the nitriles are not exposed for a long time to contact with the simultaneously formed hydrogen chloride.

25 Claims, 1 Drawing Figure

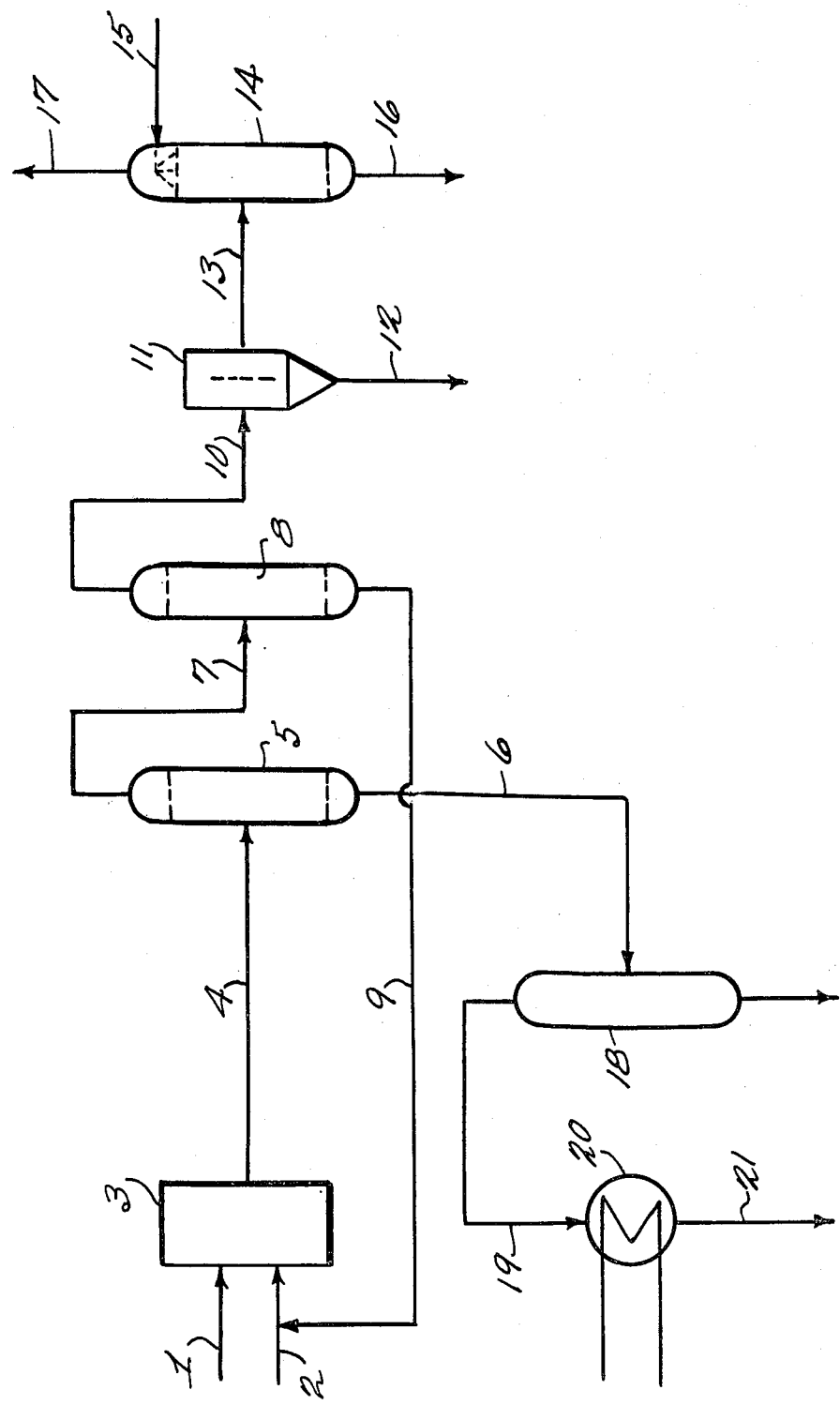

PROCESS FOR THE RECOVERY OF PURE NITRILES

BACKGROUND OF THE INVENTION

Aryl acetonitriles are produced by reaction of cyanogen chloride and aromatic or heteroaromatic methylene or methyl compounds which contain an active hydrogen at a temperature of 500° C. up to 1200° C., Grimm, Menting, Ind. Eng. Chem. Prod. Res. Div. Vol. 14 (1975), No. 3, pages 158–161 as well as Dixon U.S. Pat. No. 2,553,404 and Dixon U.S. Pat. No. 2,606,917.

Further compounds which can be produced by reaction of cyanogen chloride and corresponding methyl or methylene compounds are proposed in German OS No. 2854210 and related Schalke U.S. application Ser. No. 102,933 filed Dec. 12, 1979, abandoned.

The entire disclosures of Grimm, U.S. Pat. Nos. 2,553,404 and 2,606,917 and German OS No. 2854210 and related Schalke U.S. application Ser. No. 102,933 are hereby incorporated by reference and relied upon. More especially, the present invention can be employed to prepare aromatic or heteroaromatic nitriles from any of the aromatic or heteroaromatic methylene or methyl compounds mentioned in the disclosures relied upon.

In the production of nitriles according to the process referred to above there is the difficulty of isolating the product from the hot reactor gases in a simple way and avoiding loss of the product and excess or unreacted starting materials. There must be a quick separation or neutralization of the hydrochloric acid formed.

In the article of Grimm and Menting (Loc. cit.) which besides the production of phenylacetonitrile also is concerned with phenylmalonodinitrile there is described two different methods for the isolation of phenylacetonitrile from the reaction mixture.

The precipitation of the fine gas mist formed in the condensation with simply cooling using a reflux condenser, see Grimm and Menting (loc. cit.), is only very incomplete. The reason is that with this method the hydrochloric acid cannot be neutralized and as a result there can be caused decomposition of the product and starting material.

Thereby the direct distillation of the reaction gas mixture formed with phenylacetonitrile does not lead to a color stable product. Also the conversion of this nitrile into a color stable acetate could only be carried out with technical difficulties.

Likewise there occur difficulties in collecting the reaction gases in a methanol bath since a part of the nitrile is changed into the corresponding ester.

In Dixon U.S. Pat. No. 2,553,404 and Dixon U.S. Pat. No. 2,606,917, in principle there is condensation in the same way. In U.S. Pat. No. 2,606,917 there is formed in the reactor with the jointly fed steam in the condensation a concentrated hydrochloric acid which attacks the product and partially saponifies it.

For these reasons the yields stated in these patents are clearly lower than in the other known processes.

Water or water containing cooling agents are also employed as a direct condensation agent, see German OS No. 2854210 and Schalke U.S. application Ser. No. 102,933. The aqueous hydrochloric acid formed thereby, however, can be strongly corrosive to the apparatus and also can act saponifyingly on the product formed. For this reason the reaction gas mixture should then be simultaneously neutralized during the cooling according to this proposal.

In German OS No. 2854210 and related Schalke U.S. application Ser. No. 102,933, it is recommended that the gas mixture leaving the reactor be cooled or quenched to a temperature below 100° C. and therewith the gas condensed. It should also be favorable according to this for the purpose of quicker cooling to inject into the gases a cooling agent, preferably water. In this case, the water can contain basically acting materials such as alkali hydroxide, alkali carbonate or alkali bicargonate, for the neutralization of the hydrochloric acid formed in the reaction. However, difficulties occur hereby through the waste water formed which still contains highly toxic materials, as e.g. starting material dissolved in water, product, unreacted cyanogen chloride, by-products and decomposition products of the reaction. These toxic materials are difficult to eliminate.

The cooling agent is generally injected into the reaction gas. For better distribution therein and quicker cooling of the reaction gas there additionally is the danger of clogging of a nozzle by the carbon black particles present in the condensed product or by solid neutralization products. The chloride containing solution, formed at the point of injection at elevated temperature in the use of water or water containing cooling agent, can also lead to corrosion problems. These cannot be overcome or can only be overcome with difficulty with the metallic work materials needed at this place.

Furthermore very disadvantageous in the industrial recovery of the nitrile is the fact that the nitriles which are sensitive to hydrochloric acid in the previously customary distillative working up of the crude reaction mixture are present over long periods of time with the hydrochloric acid or hydrogen chloride formed.

Only after distillation of the reactants employed in addition to cyanogen chloride, which reactants are employed in two or threefold excess is the distillation of the nitrile formed begun. In the meantime, however, the nitrile itself already is attacked to a considerable degree. Additionally, the respective reactant with cyanogen chloride generally is more thermally stable than the nitrile formed from it.

Thus in this method of operation both the yield as well as the purity of the isolated product and also the recovery of the starting material are hurt; besides there is formed a higher portion at the distillation sump.

The known methods of condensation thus lead to losses of material or to industrial difficulties in the recovery of the nitrile concerned from the reaction gas mixture.

SUMMARY OF THE INVENTION

The object of the invention therefore is to develop a simple industrial process for the condensation of the reactor gas and therewith to increase the yield of nitrile.

It has now been found that the nitriles produced in the reaction of cyanogen chloride with aromatic or heteroaromatic methylene compounds or methyl compounds which contain active hydrogen can be recovered with an improved method of isolation and in higher yields from the reaction gas if the reaction gas resulting from the reaction at 500°–1200° C. is condensed in several successive temperature steps in which the first temperature step is the highest and the last temperature step is the lowest and the condensate obtained in each case is separately worked up.

The nitriles can be recovered in very favorable manner from the reaction gas mixture if the reaction gas is fractionally condensed in the successive steps in such manner that (1) the reaction gas is introduced, in given case in concurrent flow with an inert gas, e.g., carbon dioxide, argon, helium, or nitrogen, in a first condensation step whose temperature drop is between the boiling point of the methylene or methyl compound employed and the boiling point of the nitrile formed in the reaction, (2) the condensed crude nitrile drawn off as sump product, (3) the non-condensed portion, which in the main consists of the unreacted methyl or methylene compound and cyanogen chloride as well as of the hydrogen chloride and byproducts formed during the reaction, is supplied to a second condensation step where the temperature drop is between room temperature and the boiling point of the methyl or methylene compound, (4), the second condensate obtained thereby of residual methyl or methylene compound is drawn off and (5) preferably the waste gas of hydrogen chloride and in a give case inert gas obtained introduced into a third condensation step in which the hydrogen chloride and in a given case the inert gas is separated at a temperature of $+10°$ C. to $-100°$ C., preferably at $-10°$ to $-70°$ C., from small residues of organic impurities (6), whereupon the crude nitrile obtained in the first condensation step is distilled in known manner and in a given case further purified in known manner (7), the condensate obtained in the second condensation step preferably returned into the reaction step for the production of nitrile (8) and preferably the hydrogen chloride from the gas leaving the third condensation step recovered by washing with water.

Cyanogen chloride and its respective reactant, as in the known process, are employed in the form of gases, likewise in the known molar ratios, e.g. 1:1 to 1:6. If inert gases are used during the fractionation there are especially used as these nitrogen and carbon dioxide.

As reactants for the cyanogen chloride there are employed aromatic or heteroaromatic methylene or methyl compounds which contain an active hydrogen and do not form a hydrochloride with hydrochloric acid.

For the process of the invention there are thus suited toluene derivatives substituted on the nucleus. As substituents there are included hydrogen, halogens such as fluorine and/or chlorine (and/or bromine), additionally methyl groups, hydroxy groups or nitrile groups.

The substituents can be chosen in the o-, m-, or p- positions to the methyl group of the toluene to form corresponding derivatives. The hydroxy group is present as a substituent only in the p-position.

Commonly as substituents with toluene there can be present fluorine and chlorine or two methyl groups in the 3 and 5 positions to the methyl group already present.

When hydrogen is the substituents naturally the compound is toluene itself.

Furthermore, there have proven as suited nuclear substituted methyl thiophenes. Particularly to be considered are 2-methyl thiophene, 3-methyl thiophene, 3,4-dimethyl thiophene.

A further compound which can be employed in the process of the invention is diphenylmethane.

Prefered are:
toluene, o-xylene, m-xylene, p-xylene, o-fluorotoluene, m-fluorotoluene, p-fluorotoluene, p-cresol, 2-methyl thiophene, and 3-methyl thiophene, p-cyanotoluene is also usable.

Additional starting compounds include o-chlorotoluene, m-chlorotoluene, p-chlorotoluene, 1-methyl naphthalene, 2-methyl naphthalene, 1,3,5-trimethyl benzene, m-cyanotoluene, o-cyanotoluene, 2-fluro-4-chlorotoluene, 2,6-dimethyl naphthalene, 2,3-dimethylthiophene, 2-benzylthiophene, 3-benzylthiophene, 5-chloro-2-methylthiophene, 2,2'-dithienylmethane, 3-phenoxytoluene, 2-phenoxytoluene, 4-phenoxytoluene, 4-methoxytoluene. 2,3-dimethylnaphthalene, 2-fluoro-5-chlorotoluene, 2-fluoro-6-chlorotoluene, 2-chloro-4-fluoro-toluene, 1,2,4,5-tetramethyl benzene, and 2,4-dichlorotoluene.

As stated in the above-mentioned Schalke patent, the process of the invention is suited for the production of aromatic or heteroaromatic acetonitriles of the general formula

$$R_1—\underset{\underset{R_2}{|}}{CH}—CN \qquad (I)$$

in which $R_1$ is particularly a hydrogen atom or a phenyl or thienyl group and in which $R_2$ particularly is a phenyl, naphthyl or thienyl group which in a given case can have one or more substituents which can be the same or different. These substituents especially can be halogen atoms, preferably fluorine or chlorine atoms, or methyl, hydroxyl or cyano groups. Other substituents include aryloxy and methoxy.

Preferably with the products obtained according to the process of the invention, it is a matter of forming substituted phenylacetonitrile or thiopheneacetonitrile or diphenylacetonitrile from the corresponding starting material.

There are used for the first and second condensation steps known fractionating columns which contain various kinds of plates or packings, preferably Sambay or falling film evaporators. Preferably the reaction mixture is led precooled into the first step. For the establishment of the desired temperature, e.g. a thermostatic fluid is used in the double jacket of the column or falling film evaporator which in the first condensation step should not go below 80° C. as the lowest temperature and should not exceed 200° C.

Corresponding temperatures are valid for the second and third condensation steps, i.e. in the second step the temperature of the liquid should not go below 20° C. or above 82° C.; in the third step it should not go below $-100°$ C. or above $+50°$ C.

As thermostatic fluid in the first condensation step there can even be used steam for hot temperatures above 100° C. Generally for this temperature range there are employed the known oils for this purpose.

The optimum temperature for the operation of the fractionating columns in the individual condensation steps are established with the help of analytical measurements in a preliminary test, since as is known they depend on customary column parameters such as height, diameter, type of packing or plates (if present), amounts fed in and flow velocities of the condensing gases.

BRIEF DESCRIPTIONS OF THE DRAWINGS

The single FIGURE of the drawings is a schematic diagram illustrating the direct fractionation of the reaction gases.

DETAILED DESCRIPTIONS

Referring more specifically to the drawings there are supplied to the reactor 3 cyanogen chloride via line 1 and the reaction partner via line 2 and the reactants are reacted in the reactor.

The nitrile containing gas leaves the reactor 3 and enters the fractionating column 5 via the cooled line 4. The separation into crude nitrile which is drawn off via line 6 and gaseous reaction partner takes place in the fractionating column. The gaseous reaction partner together with the likewise gaseous hydrogen chloride, unreacted cyanogen chloride and organic byproducts are drawn off at the head of the column 5 via line 7 as is led into the fractionating column 8.

Here the unreacted reaction partner and cyanogen chloride are condensed as completely as possible and are either drawn off as such (not shown) or preferably via line 9 led back into the reactor 3 for the production of nitrile.

The residual gas leaving the column 8 consists essentially of hydrogen chloride and in a given case inert gas, as well as lower boiling byproducts, such as e.g. adducts of cyanogen chloride and hydrogen chloride of unknown structure.

As shown in the drawing this residual gas is led via line 10 into the separator 11 and there is freed from the organic impurities which are drawn off as liquids via line 12 and, in case desired, can be separately worked up (the last is not shown).

The gaseous hydrogen chloride freed from impurities goes via line 13 into a washing column 14 into which water is supplied via line 15. The aqueous hydrochloric acid solution leaves the system via line 16. Depending on the amount of water supplied there can be recovered concentrated or less concentrated hydrochloric acid solutions. Also it is possible to use other washing agents such as alkaline solutions, e.g. dilute alkali liquors, e.g. sodium hydroxide or potassium hydroxide, or carbonate solutions, e.g. sodium carbonate or potassium carbonate; however, they do not lead to utilizable products such as with the use of water.

The possible use of inert gas, which leaves the system via line 17, for working up the reaction gas is not shown.

The crude nitrile leaving the fractionating column 5 via line 6 enters the fractionating column 18 from which the pure nitrile in vapor form is drawn off via line 19 and is condensed in condenser 20. The product is drawn off via line 21.

There are used for the first and second condensation steps 5 and 8 known fractionating columns which contain various plates or packings, preferably Sambay or falling film evaporators. They are operated under apparatus pressure, preferably normal pressure. The third condensation step 11 generally consists of a heat exchanger which is operated with cooling brine. This heat exchanger can be connected before or behind with an activated carbon filter for the better adsorption of the byproducts. In place of activated carbon there can also be used other adsorption agents.

The process permits the direct isolation of the nitrile formed in the reaction with increase of the yield, furthermore, the direct isolation of the starting material employed in excess, which then can be immediately recycled in a cyclic process, in a given case with the residue of cyanogen chloride therein which have not reacted in the reaction, as well as the recovery of hydrochloric acid solutions. If the hydrochloric acid solutions are used again then there is no waste water.

Unless otherwise indicated all parts and percentages are by weight.

The process can comprise, consist essentially of or consist of the steps set forth with the stated materials.

EXAMPLE I

Phenylacetonitrile From Toluene 86.1 grams (1.4 moles) per hour of gaseous cyanogen chloride were fed via line 1 and 561 grams (6.1 moles) of gaseous toluene as well as 1 to 2 liters of gaseous nitrogen per hour were fed via line 2 into the heated reactor 3 of about one meter and having a diameter of 55 mm and an average temperature of 680° C. The nitrile containing gas from the reactor 3 enters the column 5 via the cooled line 4. The column 5 via consists of a "Sambay Evaporator" with an internal surface area of 0.1 m$^2$ and a packed column 20 cm long placed thereon. Hot oil flows through the double jacket of column 5. At the foot of the column there were led in 2 to 3 liters of gaseous nitrogen, the temperature of the oil in the double jacket is so regulated that the phenylacetonitrile condensing in the foot of this column and having a temperature of about 140° C. can be drawn off via line 6, while the waste gas at the top of the column having a temperature of about 120° C. is led via line 7 into the fractionating column 8. The column 8 has a length of 50 cm a diameter of 2 cm and is filled with Raschig rings. At the foot of the column there is led in per hour about 2-3 liters of gaseous nitrogen. The outer cooling is so regulated over the double jacket that there prevails at the foot of the column a sump temperature of 110° C. and at the head of the column a temperature of 20°-40° C. The toluene condensed in column 8 with the residues of cyanogen chloride contained therein is drawn off via line 9, returned to line 2 and mixed with fresh toluene for supplementing the consumed material led into the reactor 3.

The residual gas leaving the column 8 is led into a separator 11 consisting of a cooling trap held at 30° C. and via line 13 through an activated carbon filter into a washing column 14 in which there takes place the washing of the residual gases with water. There are obtained in column 5 per hour 146.9 grams of crude product from which 1.8 grams of a o-toluonitrile were separated by distillation in column 18 at 70° C./3 mm. Subsequently, there were distilled at 85° C./3 mm 142.4 grams of pure phenylacetonitrile having a purity of 99%. This corresponds to a yield of 86% based on the cyanogen chloride employed.

There accumulated in the column 8 429.4 grams of solution per hour. A purity of about 99% was ascertained for the toluene recovered. There was detectable about 0.4% of cyanogen chloride. Therewith, there was calculated a yield of 84% based on the toluene.

The titration of the aqueous solution of the gas washer with caustic soda solution against methyl orange as the indicator gave a HCl content which corresponds to 98.5% of the hydrochloric acid found from the cyanogen chloride.

In the comparison example the reworking was with the methanol free condensation method of "Grimm and Menting".

Comparison Example

There were fed into the same reactor 3 at 680° C. via line 1 86 grams (1.4 moles) per hour of gaseous cyanogen chloride and via line 2 561 grams (6.1 moles) of gaseous toluene and 2 liters of gaseous nitrogen per hour. The product gas was led from the reactor 3 into a three necked flask cooled by a water bath and equipped with a reflux condenser. The waste gas leaving the reflux condenser was led via the separator 11 into the washing column 14.

By condensation of the reaction gas there was obtained per hour 584.4 grams of solution in the flask and in the separator which was worked up by fractional distillation.

From a one hour experiment there were recovered 397.5 grams of toluene at a boiling temperature of 110° C. Subsequently, there were recovered by distillation at 70° C./3 mm 5.2 grams of o-toluonitrile. Then there distilled 131 grams of phenylacetonitrile at 85° C./3 mm.

As distillation sump there remained 44.2 grams. Therewith, there was calculated a yield of 79.9% based on the cyanogen chloride and 62.9% based on the toluene.

In the distillation there were driven out of the solution a not inconsiderable amount of hydrochloric acid as well as cyanogen chloride. The titration of the contents of the washing column 14 with caustic soda solution against methyl orange as indicator gave an HCl content which only corresponds to 62.3% of the hydrochloric acid formed from the cyanogen chloride.

EXAMPLE 2

Thiophene-3-acetonitrile From 3-methylthiophene

There were fed into the reactor heated to 710° C. per hour 49.2 grams (0.8 mole) of gaseous cyanogen chloride, 314.1 grams (3.2 moles) of gaseous 3-methylthiophene and 2 liters of nitrogen. There were drawn off at the foot of the column 5 the crude product at about 135° C. and distilled in the fractionating column 18. There were obtained in the column 5 per hour 88.1 grams of crude product, from which there were obtained in the column 18 by distillation at 115°–120° C./12 mm 83.4 grams of thiophene-3-acetonitrile having a purity of 98%. This corresponds to a yield of 82.9% based on the cyanogen chloride employed.

The waste gas of the column 5 was led at about 120° C. into the column 8. The 3-methylthiophene condensed in the column 8 was drawn off at a sump temperature of 110° C. and return to the reactor with the residual cyanogen chloride contained therein and fresh 3-methylthiophene for supplementing the material used up. In the column 8 there were obtained per hour 236.5 grams of solution. It consisted of 98.3% 3-methylthiophene and contained about 0.6% of cyanogen chloride. Therewith, there was calculated a yield of 79.8% based on the 3-methythiophene.

The residual gas leaving the column 8 was led via line 10 into a separator held at 30° C. and then into a washing column 14. The titration of the aqueous solution of this gas washer with caustic soda solution against methyl orange as indicator gave an HCl content which corresponds to 96.2% of the hydrochloric acid formed from the cyanogen chloride.

Comparison Example

The reactor was operated in the same manner as in Example 2 but with the quenching apparatus of the Comparison Example 1 (phenylacetonitrile). There were obtained per hour 324.6 grams of solution which was worked up by fractional distillation.

From a one hour experiment there were recovered at a boiling temperature of 114°–116° C. 221.5 grams of 3-methylthiophene. Subsequently, there were recovered through vacuum distillation at 115°–120° C./12 mm 77.4 grams of thiophene-3-acetonitrile having a purity of 98%. As distillation sump there remained 25.1 grams. Therewith, there was calculated a yield of 77% based on the cyanogen chloride and 65.3% based on the 3-methylthiophene. The titration of the contents of the washing column gave an HCl content which only correspond to 47.3% of the hydrochloric acid formed from the cyanogen chloride.

EXAMPLE 3

Thiophene-2-acetonitrile From 2-methylthiophene

There was used the same apparatus as is described in Example 1.

There were fed into the reactor heated to 690° C. per hour 86 grams (1.4 moles) of gaseous cyanogen chloride, 549 grams (5.6 moles) of gaseous 2-methylthiophene as well as 1–2 liters of gaseous nitrogen.

There were obtained in the column 3 per hour 155.9 grams of crude product having a temperature of 135° C., from which there was recovered after distillation in the column 18 at 113°–115° C./11 mm 148 grams of thiophene-2-acetonitrile having a purity of 98%. This corresponds to a yield of 84.2% based on the cyanogen chloride employed.

The gas passing over into the column 8 at 115° C. was condensed here, whereby there were obtained 397 grams of solution per hour having a temperature of 110° C. The solution consisted of 99% 2-methylthiophene and still contained 0.5% of cyanogen chloride. Therewith, there was calculated a yield of 75% based on 2-methylthiophene. The solution was immediately returned into the reactor.

The titration of the contents of the gas washer gave an HCl content which corresponds to 95.3% of the hydrochloric acid formed from the cyanogen chloride.

Comparison Example

In carrying out the comparison example analogous to Comparison Examples 1 and 2, there were able to be obtained 405.7 grams of 2-methylthiophene having a purity of 99%, 118.1 grams of thiophene-2-acetonitrile having a purity of 98% and 42 grams of distillation sump. The titration gave a HCl content of 53.2%, calculated as a yield of 68.6% based on the cyanogen chloride and 65.6% based on the 2-methylthiophene.

EXAMPLE 4

4-Methylphenylacetonitrile From 1,4-dimethyl benzene

There were fed into a 110 cm heated reactor 3 having a diameter of 60 mm and an average temperature of 720° C. via line 1 per hour 53.4 grams of cyanogen chloride and via line 2 386 grams of gaseous 1,4-dimethyl benzene as well as 1–2 liters of gaseous nitrogen. The product containing gas leaving the reactor entered into column 5 via the cooled line 4. The 4-methylphenyl acetonitrile condensing in the column 5 was withdrawn at a temperature of about 170° C. via line 6 and led to the column 18 for vacuum distillation.

At the head of the column 5 the waste gas having a temperature of about 150° C. was led via line 7 into the column 8. The 1,4-dimethyl benzene with the residues of cyanogen chloride contained therein condensing in the column 8 was drawn off at a temperature of 110° C. and treated with fresh material returned into the reactor. The residual gas leaving the column 8 was led via separator 11 to the wash column 14.

There was obtained in the column 5 per hour 96.3 grams of crude product from which there were obtained by distillation in the column 18 at 92°–95° C./3 mm 90.7 grams of 4-methylphenylacetonitrile having a purity of 98%. This corresponds to a yield of 78% based on the cyanogen chloride employed.

There were obtained in the column 8 per hour 290.4 grams of 1,4-dimethyl benzene having a purity of 99% and 0.3% cyanogen chloride content. Therewith, there is calculated a yield of 73% based on 1,4-dimethyl benzene. The titration of the aqueous solution of the gas washer gave an HCl content of 97.3%.

In the Comparison Example there was obtained a yield of 77% based on the cyanogen chloride and 66% based on the 1,4-dimethyl benzene.

EXAMPLE 5

4-Hydroxybenzylcyanide From p-cresol

There were fed into the 1 meter heated reactor having a diameter of 55 mm and an average temperature of 720° C. via line 1 per hour 46.1 grams (0.75 mole) of gaseous cyanogen chloride and via line 2 313.6 grams (2.9 moles) of gaseous p-cresol as well as 1–2 liters of gaseous nitrogen. From the reactor 3 the nitrile containing gas entered into column 5 via the cooled line 4. The column 5 consisted of a "Sambay-Evaporator" having an inner surface area of 0.1 m and an erect packed column 20 cm long. At the foot of the column there were fed in per hour 2–3 liters of gaseous nitrogen, the temperature of the oil in the double jacket of the column is so regulated that the crude product condensing in the column and having a temperature of about 180° C. can be withdrawn via line 8, while at the head of the column 5 the waste gas having a temperature of about 160° C. is led via line 7 into the fractionating column 8. The column 8 has a length of 50 cm, a diameter of 2 cm and is filled with Raschig rings. At the foot of column 8 per hour there were led in about 2–3 liters of gaseous nitrogen. The cooling over the double jacket is so regulated that at the foot of the column there prevails a sump temperature of up to 120° C. and at the column head a temperature of 20°–40° C. The p-cresol condensing in the column 8 contains 5–6% phenol. Only after distillation separation of the phenol can be recovered p-cresol mixed with fresh p-cresol for replacement of material consumed be returned into the reactor 3. The residual gas leaving the column 8 is led via line 10 into the separator 11 at −30° C., as well as to the activated carbon filter (not shown) and thereupon led into the washing column 14 in which there takes place the washing of the residual gas with water. There are obtained in the column 5 per hour 91.6 grams of crude product from which there is obtained by distillation in the column 18 at 160° C./1 Torr 54.9 grams of p-hydroxyphenylacetonitrile. This corresponds to a yield of 55% based on the cyanogen chloride employed.

There are obtained per hour in column 8 233.8 grams of solution. This solution consists of 94.6% p-cresol and 5.4% of phenol. Therewith, there is calculated a yield of 48.2% based on the p-cresol. The titration of the aqueous solution of the gas washer with caustic soda solution against methyl orange as indicator gave a HCl content which corresponds to 91.2% of the hydrochloric acid formed from the cyanogen chloride.

The entire disclosure of German priority application P No. 3006 424.5 is hereby incorporated by reference

What is claimed is:

1. In a process for the recovery of a nitrile prepared by reacting at 500°–1200° C. cyanogen chloride with an aromatic compound or heteroaromatic compound containing a methyl group or a methylene group containing an active hydrogen and working up the reaction gas mixture, the improvement comprising condensing the reaction mixture of several successive temperature steps in which the first temperature step has the highest temperature and the last temperature step has the lowest temperature, the first condensation step having a drop in temperature to between the boiling point of the methylene or methyl compound employed and the boiling point of the nitrile, thereby condensing the nitrile as a first condensate, drawing off the condensed crude nitrile as sump product, supplying the non-condensed portion which consists chiefly of unreacted methyl or methylene compound and cyanogen chloride as well as hydrogen chloride to a second temperature step between room temperature and the boiling point of the methyl or methylene compound, thereby condensing the residual methyl or methylene compound as a second condensate and drawing off the second condensate.

2. The process of claim 1 wherein the reaction is carried out at 550° to 850° C.

3. The process of claim 1 wherein the nitrile formed has the formula:

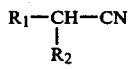

where $R_1$ is hydrogen, phenyl, naphthyl or thienyl and $R_2$ is phenyl or thienyl or is a substituted phenyl, naphthyl, thienyl or group having at least one substituent wherein the substituent is lower alkyl, halogen, hydroxy, cyano, acyloxy, aryloxy or methoxy and that the starting methyl or methylene compound has the formula:

4. The process of claim 3 wherein $R_1$ is hydrogen and $R_2$ has a methyl group attached to phenyl, thienyl or naphthyl and in addition has 0 to 2 additional substituents selected from the group consisting of lower alkyl, hydroxy, cyano, halogen, and phenoxy.

5. The process of claim 4 wherein $R_1$ is hydrogen and $R_2$ is methyl phenyl having 0 to 3 further substituents selected from the group consisting of methyl, ethyl, halogen, hydroxy, cyano and phenoxy, methyl naphthyl having 0 to 2 further substituents selected from the group consisting of methyl, ethyl and halogen and methylthienyl having 0 to 1 methyl substituent.

6. The process of claim 5 wherein $R_2$ is mono to tetramethylphenyl.

7. The process of claim 5 wherein $R_2$ is phenyl having 1 to 2 ring halogen atoms selected from the group consisting of chlorine and fluorine.

8. The process according to claim 5 wherein $R_2$ is phenyl having one ring hydroxy group.

9. The process according to claim 5 wherein $R_2$ is phenyl having one ring cyano group.

10. The process according to claim 5 wherein $R_2$ is phenyl having one additional methyl group and one fluorine or chlorine on the ring.

11. The process according to claim 5 wherein $R_2$ is methylthienyl having 0 to 1 additional methyl group attached to the ring.

12. The process according to claim 3 wherein $R_1$ is phenyl or thienyl and $R_2$ is phenyl or thienyl.

13. The process according to claim 12 wherein $R_1$ is phenyl or thienyl and $R_2$ is phenyl or thienyl.

14. The process according to claim 12 wherein $R_1$ is phenyl and $R_2$ is thienyl.

15. The process according to claim 12 where $R_1$ and $R_2$ are both phenyl.

16. The process of claim 3 wherein the starting compound is toluene, o-xylene, m-xylene, p-xylene, o-fluorotoluene, m-fluorotoluene, p-cresol, 2-methylthiophene, 3-methylthiophene, or diphenylmethane.

17. The process of claim 16 wherein the starting material is toluene, 2-methylthiophene, or 3-methylthiophene.

18. The process of claim 3 wherein the starting compound is p-cyanotoluene.

19. The process of claim 1 comprising condensing in a third condensation step the waste gas from the second condensation step and containing hydrogen chloride with or without inert gas at a temperature of +10° C. to −100° C. and thereby removing residual organic impurities therefrom.

20. The process of claim 19 wherein the third condensation step is carried out at −10 to −70° C.

21. The process of claim 1 comprising distilling the crude nitrile obtained in the first condensation step to purify it.

22. The process of claim 1 comprising returning the condensation from the second condensation step to the reactor for forming further nitrile.

23. The process of claim 1 including the step of recovering the hydrogen chloride subsequent to the second condensation step as hydrochloric acid by washing the waste gases with water.

24. The process of claim 19 including the step of recovering the hydrogen chloride after the third condensation step as hydrochloric acid by washing the waste gases with water.

25. The process of claim 24 including the steps of distilling the crude nitrile obtained in the first condensation step to purify it and returning the condensate from the second condensation step to the reactor for forming further nitrile.

* * * * *